United States Patent
Sang et al.

(10) Patent No.: US 10,486,412 B1
(45) Date of Patent: Nov. 26, 2019

(54) 3D BIO-PRINTER

(71) Applicant: Taiyuan University of Technology, Taiyuan Shi, Shanxi Sheng (CN)

(72) Inventors: Shengbo Sang, Taiyuan (CN); Zhongyun Yuan, Taiyuan (CN); Hulin Zhang, Taiyuan (CN); Aoqun Jian, Taiyuan (CN); Kai Zhuo, Taiyuan (CN); Xing Guo, Taiyuan (CN); Wendong Zhang, Taiyuan (CN)

(73) Assignee: TAIYUAN UNIVERSITY OF TECHNOLOGY, Taiyuan shi, Shanxi sheng (CN)

( * ) Notice: Subject to any disclaimer, the term of this patent is extended or adjusted under 35 U.S.C. 154(b) by 0 days.

(21) Appl. No.: 16/362,834

(22) Filed: Mar. 25, 2019

(30) Foreign Application Priority Data

May 10, 2018 (CN) .......................... 2018 1 0444116
May 11, 2018 (CN) .......................... 2018 1 0449399

(51) Int. Cl.
  *B33Y 30/00* (2015.01)
  *B33Y 40/00* (2015.01)
  *C12N 5/00* (2006.01)
  *C12M 1/26* (2006.01)

(52) U.S. Cl.
  CPC .............. *B33Y 30/00* (2014.12); *B33Y 40/00* (2014.12); *C12N 5/0062* (2013.01); *C12M 33/00* (2013.01)

(58) Field of Classification Search
  CPC ......... B33Y 10/00; B33Y 40/00; B33Y 30/00; B33Y 70/00
  See application file for complete search history.

(56) References Cited

U.S. PATENT DOCUMENTS

| | | | |
|---|---|---|---|
| 2003/0090034 A1* | 5/2003 | Mulhaupt | B29C 31/045 264/255 |
| 2004/0217186 A1* | 11/2004 | Sachs | B41J 2/1429 239/11 |
| 2013/0089642 A1* | 4/2013 | Lipson | A23P 20/20 426/115 |
| 2018/0230423 A1* | 8/2018 | O'Mahony | A61L 27/20 |
| 2018/0273886 A1* | 9/2018 | Akiyama | B33Y 50/00 |
| 2019/0105836 A1* | 4/2019 | Lan | B29C 64/321 |

* cited by examiner

*Primary Examiner* — Nathan A Bowers
(74) *Attorney, Agent, or Firm* — Venable LLP; Jeffri A. Kaminski

(57) ABSTRACT

A 3D bio-printer capable of detecting cell activity is provided. The 3D bio-printer includes an upper PC and a lower 3D printer. A conveying hose is connected to a printhead base of the printer, and a temperature controller is connected to the conveying hose. A printhead controller is connected to the other end of the conveying hose, a printhead is connected to the bottom of the printhead controller, and a main control cabinet controls the printhead to work via a signal generator. A prototyping table is provided under the printhead and is connected with a cell activity detecting device for detecting activity of a printed product. Cell activity can be detected in the process of printing, which ensures that the printed biological tissues maintain biological activity. It can supply multi-biological raw materials and realize multi-biological material printing, which ensures an environment suitable for biological material printing.

4 Claims, 7 Drawing Sheets

3D BIO-PRINTER

CROSS REFERENCE TO RELATED APPLICATION

This patent application claims the benefit of Chinese Patent Application No. 201810449399.X, filed May 11, 2018, and Chinese Patent Application No. 201810444116.2, filed May 10, 2018, contents of which are incorporated by reference herein.

BACKGROUND

1. Technical Field

The present disclosure relates to the technical field of biological tissue engineering, and more particularly, to a 3D bio-printer capable of detecting cell activity.

2. Introduction 3D printing is a type of rapid prototyping technology. It is a technique of constructing an object by layer-by-layer-printing based on digital model files and using powdered metal or plasticizable adhesive materials. Tissue engineering incorporates subjects such as engineering, life science, and material science. By simulating the process of human tissue and organ formation, structures having biological activity can be constructed and cultured in vitro. Among them, 3D printing technology has become the most powerful research means in the tissue engineering field because it can mold any complicated three-dimensional structure using a variety of materials. The principle of 3D printing technology is layered manufacturing, accumulated layer by layer. A conventional cell printhead mixes cells with biological materials and extrudes the mixture to form a silk-like shape, then reciprocates repeatedly to form a plane, and forms a corresponding three-dimensional structure as the planes accumulate. It is a means capable of positioning and assembling biomaterials or cell units, manufacturing medical devices, tissue engineering scaffolds, tissues and organs and the like according to the principle of material manufacturing driven by digital 3D modelling.

However, 3D bio-printing is still very different from the conventional 3D printing technology in that, in addition to the use of core technology of the conventional 3D printing, all manufacturing processes of 3D bio-printing must conform to biological standards to ensure cell activity and tissue functions, as well as conforming to medical standards, such as sterility. At present, there are many technical defects in 3D bio-printing devices, for example: (1) the cell printing speed is slow; (2) the cell printing precision is low; (3) it is difficult to detect the cell activity of printed tissues and organs in real time; (4) it is difficult to realize automation in the process of 3D bio-printing; (5) the number and type of printhead are limited, and replacement of the printheads is complicated; and (5) it is not possible to adjust printer configuration in real time according to cell activity during printing to increase printing success rate.

SUMMARY

The present disclosure overcomes the deficiencies in prior art. An object of the present disclosure is to provide a 3D bio-printer capable of detecting cell activity so as to overcome the problems of low printing precision, inability to ensure the activity of printed tissue cells, frequent replacement of printheads, etc.

In order to achieve the aforementioned object, the present disclosure adopts the following technical solutions: a 3D bio-printer capable of detecting cell activity comprises an upper personal computer (PC) and a lower 3D printer. The lower 3D printer includes a main control cabinet, a stepping motor, a signal generator, a mechanical arm, a printhead base, a printhead, a printhead controller, a prototyping table, a cell activity detection table, an air pump, an air pump control box, and an air tank.

The upper PC may be connected with the main control cabinet by wire or wirelessly. The main control cabinet controls the motion of the mechanical arm by the stepping motor, and the mechanical arm is connected to the printhead base. The printhead base is connected with a material conveying hose which is used for storing and conveying biological raw materials. A top end of the material conveying hose is connected with the air pump, the air pump control box and the air tank through a conduit, and precisely controls the speed of material feeding by a precise control of the air pressure of the air pump. A temperature controller and a temperature sensor are connected to the material conveying hose. The temperature of the material conveying hose is monitored in real time by the temperature sensor. The temperature is adjusted in time by the temperature controller to keep a suitable temperature and create a good feeding environment. The other end of the material conveying hose is connected to the printhead controller, and the printhead is connected to the lower end of the printhead controller. The discharge hole of the printhead can automatically adjust the opening size of the printhead nozzle hole according to requirements on the discharge speed. The feeding speed is precisely controlled by adjusting the air pressure of the air pump and the opening size of the printhead nozzle hole.

The main control cabinet is connected to a power clock end of the signal generator, and the output end of the signal generator is connected to the printhead controller to control the switch of the printhead. The prototyping table is positioned under the printhead, and connected with a cell activity detecting device for detecting cell activity of a printed product. After a detection at the cell activity detection device, it is determined whether the configuration of the printer is appropriate according to whether the cell activity is good or not. If the configuration is inappropriate, the cause of the inappropriateness is determined and is fed back to the printhead controller for a real-time adjustment to ensure good cell activity.

Preferably, the cell activity detecting device may include a mechanical transport arm, an operation table, a reagent kit, and a detector. The function of the mechanical transport arm is to drive the operation table through the mechanical transport arm to complete the transport of tissues and organs to be tested.

The mechanical transport arm is connected with the operation table. A circular lifting platform is provided in the center of the operation table. The function of the circular lifting platform is to immerse the tissue organ to be tested into a reagent in the kit through the lifting platform. The reagent kit and the detector are fixed on the operation table, and the detector is connected with the upper PC through a signal line.

The working principle of the detection of cell activity of the printed tissues and organs is a colorimetric method. For example, a WST-8 reagent is used and is reduced by dehydrogenase in the cell mitochondria to a highly water-soluble yellow formazan product under the action of an electron carrier 1-Methoxy PMS (phenazinium methylsulfate), where the amount of the formazan product is proportional to the amount of living cells. The amount of living cells can be reflected by measuring the absorbance value at a wavelength of 450 nm using the detector.

Preferably, the material conveying hoses and the corresponding printheads are respectively five.

Preferably, the printhead is a detachable printhead and can automatically adjust the size of the printhead nozzle hole.

Preferably, the activity detection device can form self-feedback with the printhead controller based on the printed cell activity to adjust the configuration of the printer.

The 3D bio-printer of the present disclosure is divided into two parts: an upper computer and a lower computer. The upper computer is a PC end. Various parameter settings of 3D printing can be realized through the PC end, including a minimum step value of movement in the XYZ three axes, selection of materials in each printhead, graphic setting of 3D layered printing, parameter setting and real-time status reading of the conveying hose, parameter setting and status reading of the prototyping table, display of detection status of the cell activity detection device, and display of various parameters for the operation of the 3D printer.

The lower computer part is a hardware structure part of the 3D bio-printer. The upper computer and the lower computer are connected by an Ethernet port or wirelessly, and data is transmitted by TCP/IP (Transmission Control Protocol/Internet Protocol). A user may input parameters into the upper computer according to the requirement of printing. After receiving an instruction, the upper computer decodes the instruction and then transmit it to the printhead controller for communication to drive the printer to work.

The 3D bio-printer capable of detecting cell activity disclosed in the present disclosure may include a hardware constitution system and a running logic control system, thereby overcoming the existing technical problems at present. By adding the cell activity detection table in the 3D printer work case, it is possible to measure cell activity intermittently in the process of cell printing, which solves the problem that the cell activity of the printed tissue and organ cannot be detected in real time in the process of 3D printing. In the 3D printer of the present disclosure, a plurality of printing printheads are connected to the printhead base and can provide bio-printing of various raw materials at the same time. Since the printheads are detachable, the printheads with different apertures may be replaced according to the installed biological materials to realize multi-biological material printing. In the 3D bio-printer of the present disclosure, the conveying hose is connected to the printhead base for storing raw materials required for printing. An automatic supply of raw materials is realized by the air pump and the air pump control box, thereby reducing unnecessary human operation. Through the upper computer software, the method of printing tissues and organs, optimal settings for layered printing, biological materials corresponding to the printheads, minimum moving distance of the printheads, reports of results of cell activity detections, and the actual operation status of the system in operation are set.

The present disclosure has the following beneficiary effects as compared with prior art. The 3D bio-printer capable of detecting cell activity of the present disclosure can detect cell activity in the process of printing, which ensures that the printed biological tissues maintain biological activity. It can supply multi-biological raw materials and realize multi-biological material printing, which ensures an environment suitable for biological material printing. The design of detachable printheads is convenient for replacing the printheads. The cell activity detection table can form self-feedback with the printhead controller based on the printed cell activity to adjust the configuration of the printer.

BRIEF DESCRIPTION OF THE DRAWINGS

The present disclosure will be further described below with reference to the attached drawings.

DETAILED DESCRIPTION

The technical solutions of the present disclosure will be described in detail below with reference to the embodiments, but the scope of protection is not limited thereto.

The below is a detailed description of the present disclosure with reference to specific preferred embodiments, and the specific embodiments of the present disclosure are not limited thereto. For those of ordinary skill in the art, a number of simple derivations or substitutions may be made without departing from the present disclosure. All these derivations and substitutions should be considered as belonging to the scope of protection of the present disclosure determined by the submitted claims.

Figure 1:
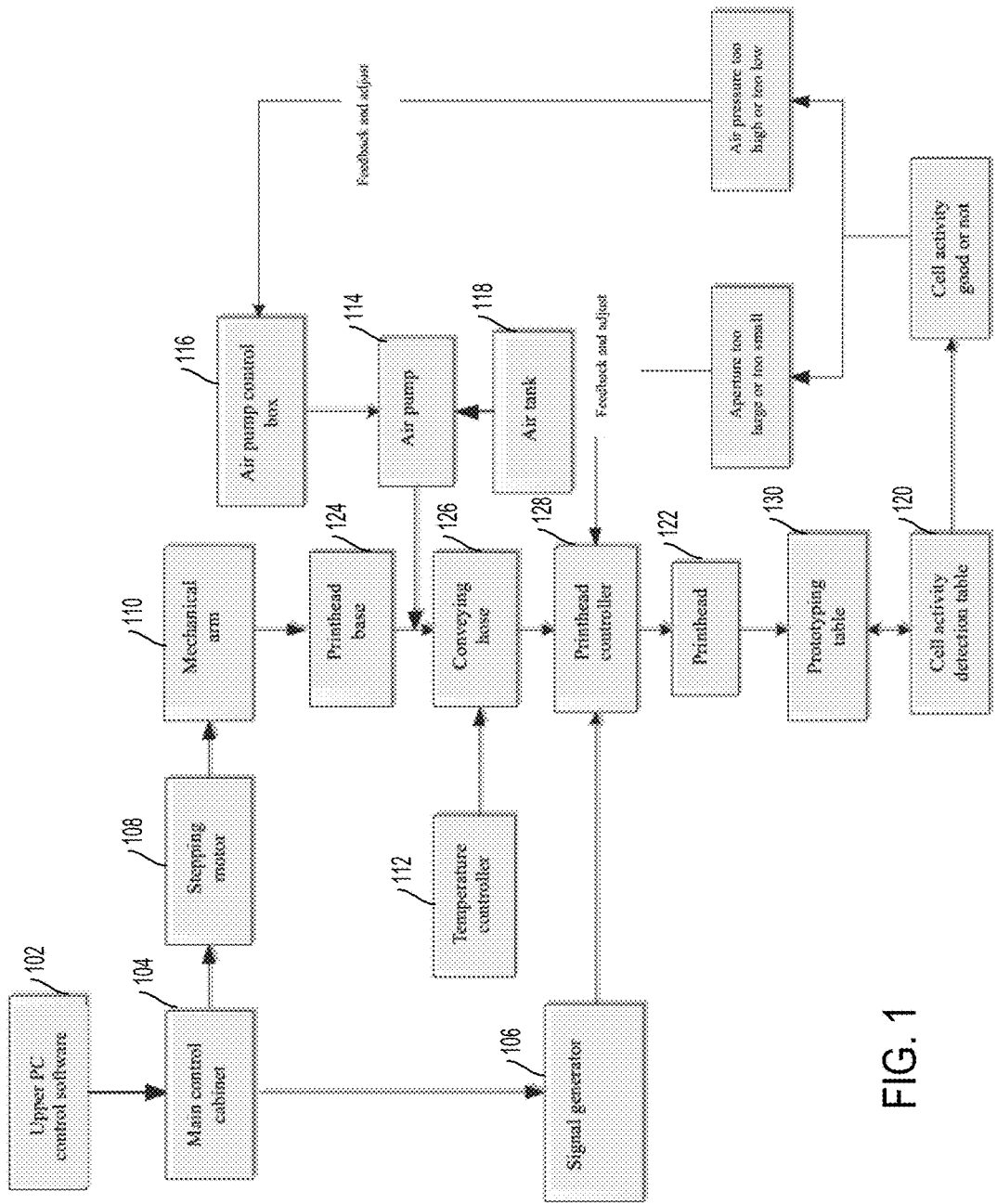
FIG. 1 illustrates a schematic structural view of a 3D bio-printing device of the present disclosure.
Figure 2:
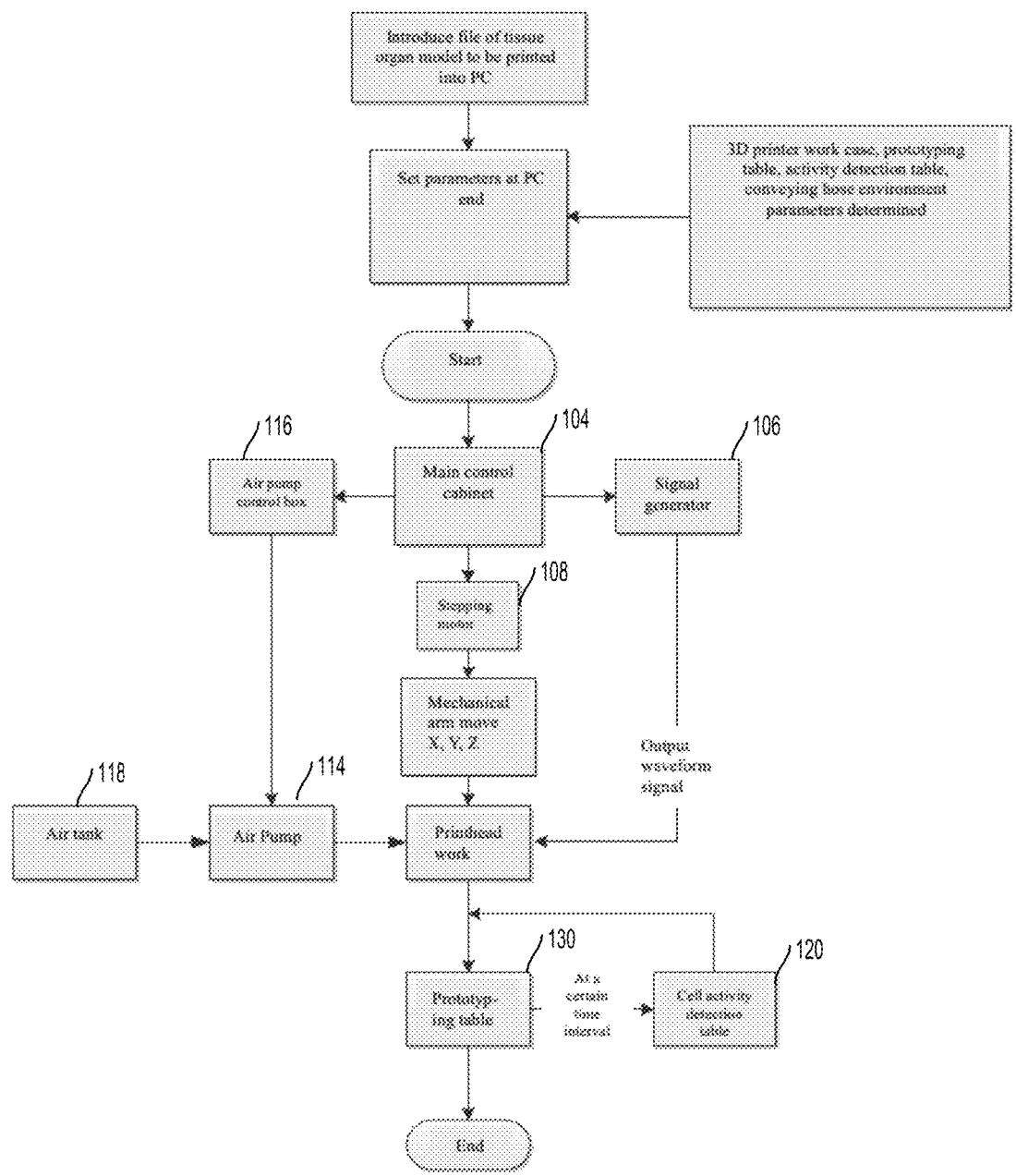
FIG. 2 illustrates a working logic diagram of the 3D bio-printing device of the present disclosure.

As shown in FIGS. 1 and 2, the 3D bio-printer capable of detecting cell activity of the present disclosure is divided into two parts: an upper computer 102 and a lower computer. The main components of the lower computer include a main control cabinet 104, a signal generator 106, a stepping motor 108, a mechanical arm 110, a temperature controller 112, an air pump 114, an air pump control box 116, an air tank 118, and a cell activity detection table 120.

A printed circuit board for single-chip microcomputer is stored in the main control cabinet 104, and a written control program is stored in a microcontroller. The microcontroller drives the peripheral hardware circuits by the control program and controls the operating part and the core algorithm part of the printer. The microcontroller also drives a programmable logic control device as a signal generator to provide various frequencies, waveforms, and output level electrical signals.

The stepping motor 108 is an open-loop control motor which converts received electrical pulse signals of different frequencies into angular displacement and linear displacement, and controls a printhead 122 to operate at different speeds and directions in the XYZ three axes.

The mechanical arm 110 is equivalent to a scaffold, and the stepping motor 108 controls the mechanical movement of the mechanical arm 110. The mechanical arm 110 is equipped with three stepping motors which respectively control the movement and the distance of movement in the X-axis direction, the Y-axis direction, and the Z-axis direction.

The 3D printer work case includes a printhead base 124 which is mounted on the mechanical arm 110 for fixing the printhead 122. The printhead base 124 is also connected with a conveying hose 126 which stores and conveys the biological raw materials required for printing.

The printhead 122 is equipped with a temperature sensor which can feed back the printing temperature of the printhead 122 in real time to ensure that the temperature of the printhead 122 is within a normal printing range. When the temperature exceeds the normal range, the temperature controller 112 may be driven in real time to adjust the temperature to keep the temperature steady.

The conveying hose 126 is connected to a printhead controller 128, and the bottom of the printhead controller 128 is connected with the printhead 122 which can print the materials onto a prototyping table 130.

The prototyping table 130 is connected with the cell activity detection table 120 for detecting cell activity of the printed tissues and organs. If the printed cell activity rate does not meet the requirements, configuration defect determination is performed. After the cause is determined, it is fed back to the printhead controller 128 to form an automatic adjustment of the configuration of the printer.

The conveying hose 126 is also connected with the temperature controller 112 which controls the temperature of the conveying hose to ensure the temperature required for the activity of the biological materials.

The air pump 114 is connected to the top of the conveying hose 126 and is also connected with the air tank 118 and the air pump control box 116 respectively. The printer can memorize the working process of printing, save the printing process in the case of power outage, and can continue printing after power-on, thereby improving work efficiency. The user at the PC end can choose to connect with the main control cabinet 104 through an Ethernet port or wirelessly.

Figure 3:
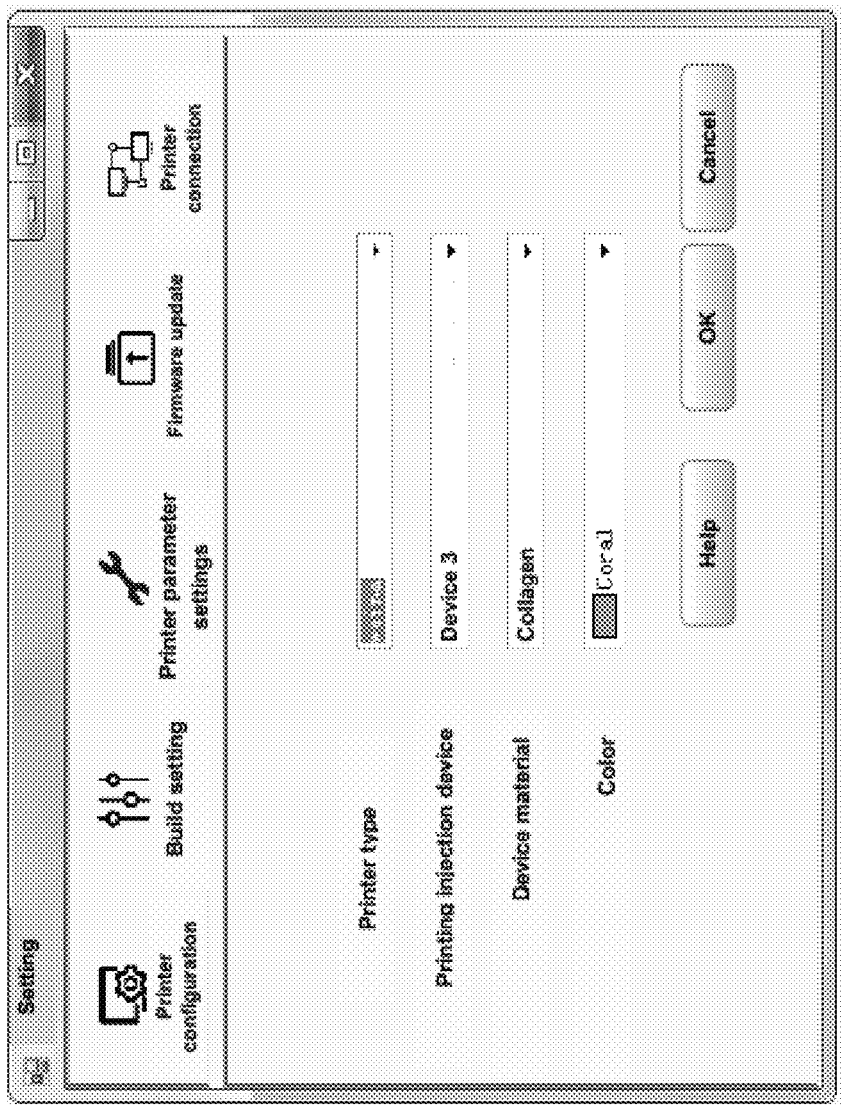
FIG. 3 illustrates a schematic diagram of a 3D bio-printing PC end of the present disclosure.

As shown in FIG. 3, an operation interface of the upper computer of the 3D bio-printer is illustrated. It is used to configure the printer on the upper computer interface, select the materials for printing and printing injection devices, and set the parameters of the printer.

Figure 4:
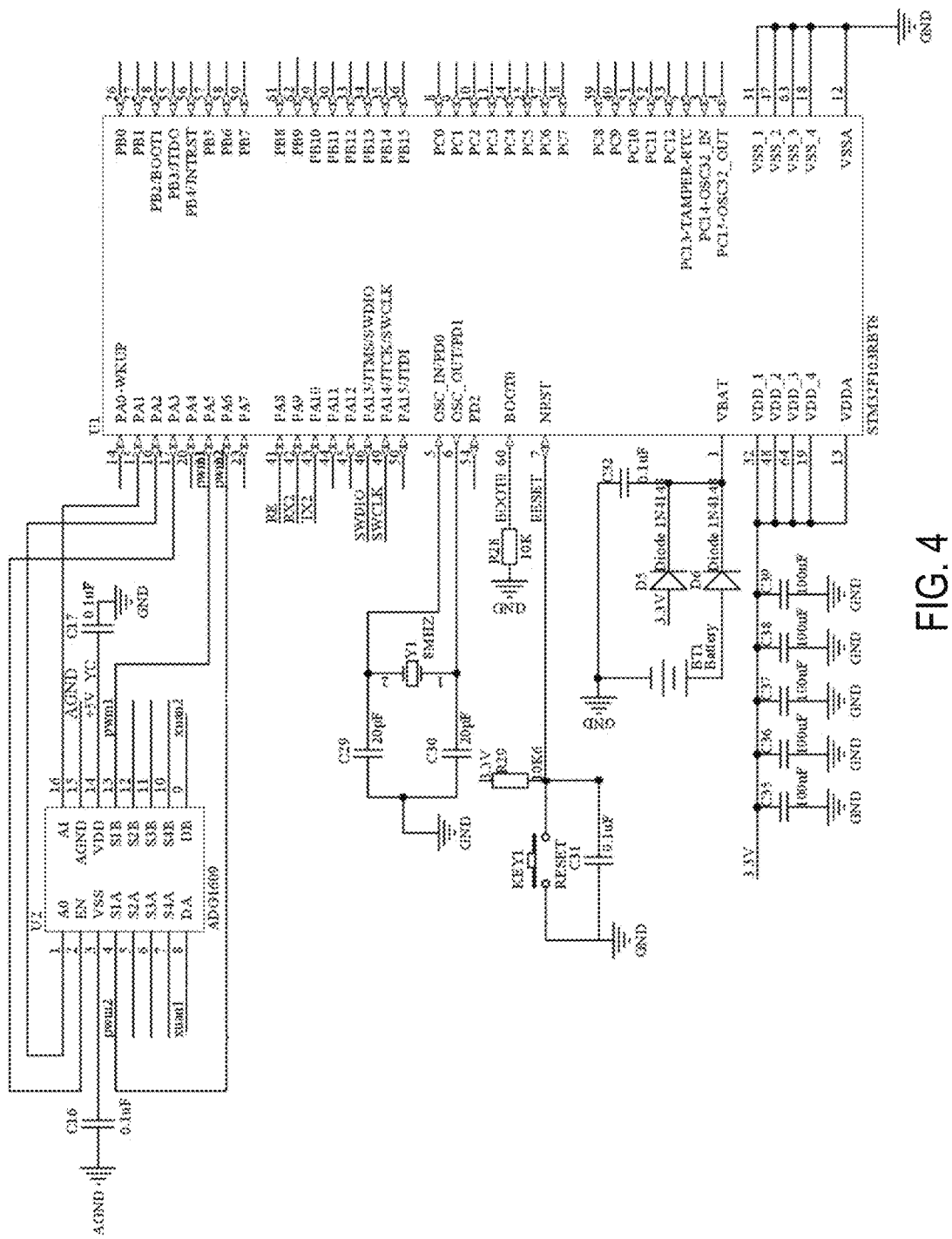
FIG. 4 illustrates an internal selection circuit diagram of a printhead controller of the present disclosure.
Figure 5:
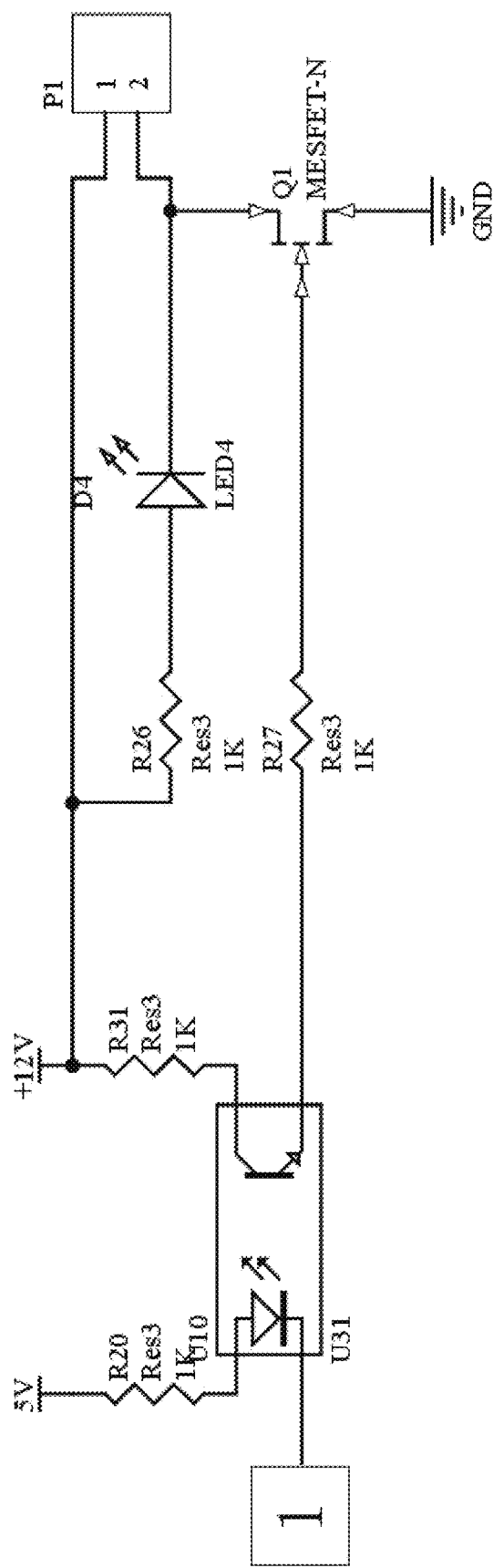
FIG. 5 illustrates a circuit diagram of a printhead temperature control module of the present disclosure.
Figure 6:
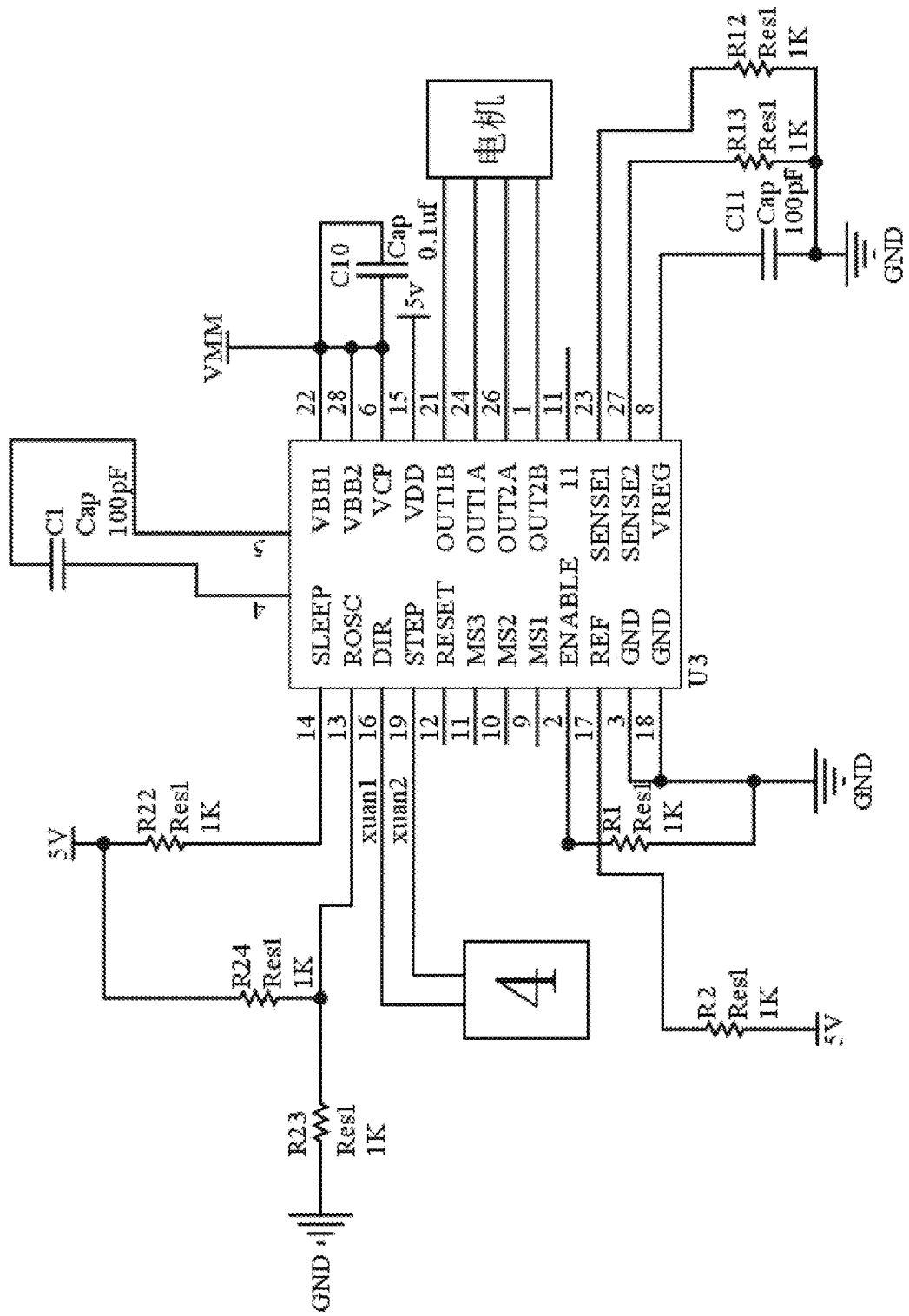
FIG. 6 is a circuit diagram of a motor drive of the present disclosure.
Figure 7:
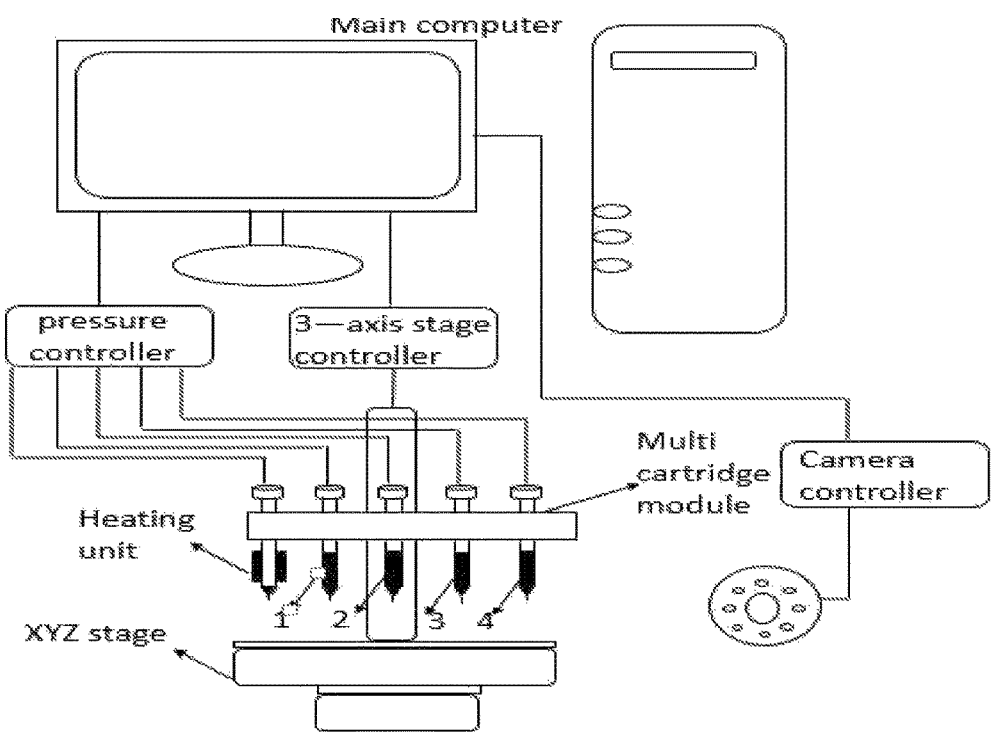
FIG. 7 illustrates an example 3D bio-printing device of the present disclosure.

FIG. 4 is an example internal circuit diagram of the printhead controller 128, which includes a control chip and a selector, and can perform the function of selecting injection devices. FIG. 5 is an example temperature control module diagram, and the temperature is adjusted through the circuit. FIG. 6 is a standard motor drive circuit performing the drive of the motor so that the motor is used to drive the movement of a printing printhead.

In the 3D bio-printing device of the embodiment, the PC end communicates with the main control cabinet by TCP/IP (Transmission Control Protocol/Internet Protocol). A user may set the work mode at the PC end according to his/her own needs. After setting, the data is sent to the main control cabinet via an Ethernet port, and the main control cabinet processes decoding and executes operations after receiving the instruction. The main control cabinet has a self-inspection function. It performs self-inspection before the operation, and prepares for work after the self-inspection verifies that the system is normal.

In some embodiments, the 3D bio-printer may use five printhead printing modes, five signal generators, three stepping motors, five printhead controllers, five air tanks, five air pumps, five conveying hoses, and five temperature controllers.

A printed circuit board for single-chip microcomputer is stored in the main control cabinet, and a written control program is stored in a microcontroller. The microcontroller drives the peripheral hardware circuits by the control program and controls the operating part and the core algorithm part of the printer. The microcontroller also drives a programmable logic control device as a signal generator to provide various frequencies, waveforms, and output level electrical signals.

The stepping motor is an open-loop control motor which converts received electrical pulse signals of different frequencies into angular displacement and linear displacement, and controls a printhead to operate at different speeds and directions in the XYZ three axes. The mechanical arm is equivalent to a scaffold, and the stepping motor controls the mechanical movement of the mechanical arm.

The mechanical arm is equipped with three stepping motors which respectively control the movement and the distance of movement in the X-axis direction, the Y-axis direction, and the Z-axis direction. Five printhead bases are installed in sequence on the mechanical arm, and two communication data by the 485 communication protocol are led out from each printhead base to return the data to the main control cabinet. The main control cabinet obtains the specific real-time position by analyzing data in the microcomputer.

The conveying hose is installed under the printhead base for storing various biological raw materials required for printing. The conveying hose is connected with a temperature sensor which can sense the temperature inside the conveying hose and adjust the temperature in real time to control the temperature inside the conveying hose for the ease of material storage. The connecting part between the printhead base and the top of the conveying hose is connected with an external air pump through a hose, and a filter screen is arranged in the middle to strictly ensure a sterile environment inside the conveying hose.

The air pump is connected with the air tank and the air tank control box, and its function is to control the air pressure difference inside the hose by controlling the running of the motor via the air pump control box according to the requirements so as to control the material feeding speed.

The conveying hose is connected to the printhead controller, and the bottom of the printhead controller is connected with the printhead. The main control cabinet is connected to a power clock end of the signal generator, and the output end of the signal generator is connected to the printhead controller. The printhead controller selects the switch corresponding to the printhead through a software driven selector, and can control the working time of the printhead by setting the time.

The printhead can be separated by this design. By connecting the printhead controller to the main control cabinet instead of directly connecting the printhead to the main control cabinet, it is only necessary to replace printheads with different apertures for replacing different biological raw materials. The printing printhead performs printing on the prototyping table. The prototyping table is connected with the cell activity detection table to form an enclosed working environment, which has a built-in high-precision temperature and humidity sensor and is a sterile environment. The tissues and organs printed on the prototyping table can be sent to the cell activity detection table for detection of the cell activity at a certain time interval. The detection time interval can be set via the upper PC end. It is determined according to the activity of the system whether the printer configuration meets the printing requirements, and if not, a feedback is formed and the configuration is automatically adjusted.

The working process of the cell activity detection table is as follows. When it reaches the detection time set at the PC end, a high-precision external timer is used for timing. When it reaches the set detection time, the main controller receives a trigger signal to control the movement of the mechanical arm to move the operation table to the prototyping table to obtain the tissue organ to be detected, and places the tissue organ on the circular lifting platform. The operation table is returned to the original position by the movement of the mechanical arm, and the tissue organ is immersed in a WST-8 reagent via the circular lifting platform. After reaction for a period of time, the circular lifting platform is raised to the original position. The operation table is moved outward by the mechanical arm, and the water-soluble yellow formazan product is subjected to light absorption detection by a detector. After the detection, the operation table is moved to the prototyping table by the mechanical arm, and the tissue organ is placed back to the original position at the prototyping table. A detection report is displayed at the PC end. The printing will continue if the detected cell activity meets the requirements. If there is a defect in the detected cell activity, the cause of the problem is determined and fed back to the controller to automatically adjust the printer configuration so as to ensure cell activity.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

We claim:

1. A 3D bio-printer capable of detecting cell activity, comprising:
    an upper PC; and
    a lower 3D printer,
    wherein:
        the lower 3D printer includes:
            a main control cabinet;
            a stepping motor;
            a signal generator;
            a mechanical arm;
            a printhead base;
            a printhead;
            a printhead controller;
            a prototyping table;
            an air pump;
            an air pump control box; and
            an air tank,
        the upper PC is connected with the main control cabinet;
        the main control cabinet controls motion of the mechanical arm by the stepping motor;
        the mechanical arm is connected to the printhead base;
        the printhead base is connected with a conveying hose which is used for storing and conveying biological raw materials;
        a first end of the conveying hose is connected with the air pump, the air pump control box and the air tank through a conduit, and controls by the air pump speed of material feeding;
        a temperature controller is connected to the conveying hose;
        a second end of the conveying hose is connected to the printhead controller;
        the printhead controller is internally designed with a selector circuit and can select a working printhead channel according to requirements;
        the main control cabinet is connected to a power clock end of the signal generator;
        an output end of the signal generator is connected to the printhead controller as a work triggering signal of the printhead controller;
        the prototyping table is provided under the printhead and is connected with a cell activity detecting device for detecting cell activity of a printed product;
        the cell activity detecting device includes a mechanical transport arm, an operation table, a reagent kit, and a detector;
        the mechanical transport arm is connected with the operation table, a circular lifting platform is provided in the center of the operation table, and the reagent kit and the detector are fixed on the operation table; and
        the detector is connected with the upper PC through a signal line.

2. The 3D bio-printer according to claim 1, wherein the conveying hose and corresponding printhead includes respectively five hoses and five printheads, and switches of printing channels are selected according to printing requirements.

3. The 3D bio-printer according to claim 1, wherein the printhead is a detachable printhead and have its temperature sensed in real time.

4. The 3D bio-printer according to claim 1, wherein after a detection at a cell activity detection table, it is determined whether configuration of the 3D printer is appropriate according to whether the cell activity is good or not, and when the configuration is inappropriate, cause of the inappropriateness is determined and is fed back to the printhead controller for a real-time adjustment to ensure good cell activity.

* * * * *